United States Patent
Gugel et al.

(10) Patent No.: US 7,435,085 B2
(45) Date of Patent: Oct. 14, 2008

(54) DENTAL TREATMENT DEVICE WITH VARIABLE COOLING

(75) Inventors: Bernd Gugel, Ulm (DE); Jorg Schopperle, Laupheim (DE)

(73) Assignee: Kaltenbach & Voigt GmbH, Biberach/Riss (DE)

( * ) Notice: Subject to any disclaimer, the term of this patent is extended or adjusted under 35 U.S.C. 154(b) by 24 days.

(21) Appl. No.: 11/233,651

(22) Filed: Sep. 23, 2005

(65) Prior Publication Data
US 2006/0063127 A1 Mar. 23, 2006

(30) Foreign Application Priority Data
Sep. 23, 2004 (DE) .................. 10 2004 046 156

(51) Int. Cl.
*A61C 1/10* (2006.01)
*A61C 3/00* (2006.01)

(52) U.S. Cl. .............................. 433/84; 433/27; 433/98
(58) Field of Classification Search ............. 433/84–85, 433/27, 98–100, 82
See application file for complete search history.

(56) References Cited

U.S. PATENT DOCUMENTS

| 2,984,008 | A |   | 5/1961 | Weisberg |
| 3,568,318 | A |   | 3/1971 | Martin |
| 4,302,185 | A | * | 11/1981 | Hall ............................ 433/27 |
| 4,373,699 | A | * | 2/1983 | Leiberich ............... 251/129.21 |
| 5,947,729 | A | * | 9/1999 | Bell ............................. 433/98 |
| 6,270,342 | B1 | * | 8/2001 | Neuberger et al. ........... 433/29 |

FOREIGN PATENT DOCUMENTS

| EP |   | 890344 A2 | 1/1999 |
| WO | WO 91/00067 |   | 1/1991 |

* cited by examiner

*Primary Examiner*—John J Wilson
(74) *Attorney, Agent, or Firm*—Fitzpatrick, Cella, Harper & Scinto

(57) ABSTRACT

In the case of a treatment device, in particular a dental treatment instrument, having a tool, such as a dental drill, driven by a drive unit, and a conduit for delivery of a cooling medium to a treatment site worked by the tool, the quantity of the cooling medium delivered to the treatment site is dependent upon the removal power of the tool or upon the torque exercised by the tool.

20 Claims, 3 Drawing Sheets

DENTAL TREATMENT DEVICE WITH VARIABLE COOLING

BACKGROUND OF THE INVENTION

1. Field of the Invention

The present invention relates to a treatment device in accordance with the preamble of claim 1, which has a tool driven by a drive unit and means for delivery of a cooling medium to a treatment site worked by the tool. In particular the present invention relates to a dental treatment instrument having a drill which can be set in rotation by a drive.

2. Description of the Related Art

In the treatment of caries or other dental treatments, working steps in which a part of the tooth substance must be removed are often unavoidable. The classical treatment tool for carrying out such work is a dental drill, which is arranged in the head region of a treatment instrument and is set into rotation by means of a drive unit. Depending on the configuration of the surface of the drill, and of the drive, there can then be set a certain material removal power. Thereby, modern dental hand instruments offer in particular also the possibility of varying the power.

In all dental treatments it is to be taken into consideration that the human tooth is a living organism which is connected with the remaining organism via the so-called tooth pulp. In the treatment of a tooth, in particular in the removal of tooth material by means of a drill, heat now arises at or in the tooth, scientific investigations having shown that at temperatures above 41° C. the tooth pulp dies off and correspondingly damage to the tooth arises.

In order correspondingly to avoid that during the treatment temperatures of more than 41° C. arise at the tooth pulp, it has long been known to deliver to the treatment site worked with the drill a cooling medium, for example, water, air or a water-air mixture. With regard to the desired cooling, cooling via a water-air mixture in the form of a spray has proved to be particularly effective, whereby as a general rule it is accepted that a cooling quantity of 50 ml per minute brings about an adequate cooling. This knowledge is again based on scientific investigations. The water-air mixture or spray is then directed at the treatment site by means of nozzles in the head region of the dental instrument.

Disadvantageous with the known spray cooling, is, however, that through this the view of the area being prepared is made worse by an aerosol mist consisting of water, air and removed particles of the tooth. This aerosol cloud, during the treatment, emerges from the mouth of the patient and contaminates the surroundings of the dental treatment station. Since the water-air mixture is further breathed in by the person carrying out the treatment, beyond this there is also an increased risk of infection.

The material removal power put to use and needed by the dentist during the treatment is subject to large variations. In order to ensure that even at the maximum removal power still usual in practice, an adequate cooling is effected, the spray quantity must correspondingly be so set that this is still adequate also for these high power ranges. This leads to the usually employed cooling quantity already mentioned above, of 50 ml water per minute.

SUMMARY OF THE INVENTION

The present invention has the object of providing an improved possibility for cooling the treatment site during a dental treatment, whereby however the disadvantages mentioned above in connection with a spray cooling are to be avoided.

This object is achieved by means of a dental treatment device having a tool driven by a drive unit and a conduit for delivering a cooling medium for a treatment site worked by the tool, wherein the quantity of cooling medium delivered to the treatment site is dependent upon the removal power of the tool or upon the torque exercised by the tool.

The solution in accordance with the invention is based on the idea of coupling the quantity of the cooling medium delivered to the treatment site to the removal power currently needed by the user of the treatment device. In accordance with the invention there is correspondingly proposed a treatment device which has a tool driven by a drive unit and means for delivery of a cooling medium to a treatment site worked with the tool, wherein the quantity of the cooling medium delivered to the treatment site is dependent upon the current removal power of the tool or upon the torque exercised by the tool.

In accordance with the present invention the maximum spray quantity is thus only delivered when it is actually needed, that is when the dentist calls upon the maximal removal power or the maximum torque. Since the dentist, however, only seldom calls upon this maximum removal power, the maximum spray quantity is only very seldom used. During the remaining treatment time, in contrast, in accordance with the invention a lesser quantity of the cooling medium is delivered.

This is of advantage in particular in the case of precision work, since with this work the removal power is very slight, in accordance with the invention correspondingly significantly lesser quantities of the cooling medium are delivered, and therewith the view of the treatment surface is less restricted. As further advantage there is provided of course that in the employment of a spray as cooling medium at the same time the undesired aerosol mist and the disadvantages connected therewith, are also reduced.

A variation of the quantities of cooling media for dental treatment instruments is already known from U.S. Pat. No. 2,984,008, but in this U.S. patent it is proposed to vary the quantity of the cooling medium in dependence upon the current speed of rotation of a dental drill. It has however been found that the coupling of the cooling medium quantity to the torque or removal power exercised is significantly more advantageous, since the speed of rotation alone is no indication of the required cooling of the treatment site. In contrast, the torque or the removal power allows direct deduction of the extent to which development of heat arises at the treatment location and to what extent correspondingly cooling is necessary. In contrast to the known method of regulation of the cooling medium, the present invention thus ensures that also in fact the currently necessary cooling of the treatment site is ensured. Dying off of the tooth substance due to insufficient cooling is correspondingly excluded.

The regulation of the quantity of the cooling medium is effected preferably by means of a control device which may be arranged either in the dental treatment instrument itself or in a supply unit for the treatment instrument. Significant components of the control device are thereby first of all detection means for detecting the removal power of the tool or the torque exercised by the tool, determination means for determining a desired quantity for the cooling medium in dependence upon the information provided by the detection means, and control and/or regulation means for setting the quantity of the issued cooling medium in dependence upon the desired quantity determined.

The present invention can be used independently of the kind of drive for the dental tool. Thus, the invention can be put to use for example in the case of electric drive motors, air turbines or air motors, wherein the configuration of the control device then differs in substance in regard to the detection means for detecting the removal power or the torque.

If, for example an electric motor is used for the drive of the drill, the torque can be detected via the motor current and the power overall via an additional detection of the motor voltage. For each instrument there is then associated with a power value the spray quantity determined in each case by scientific investigations and stored in an electronic memory within the control device as a table. By means of a comparison of the detected removal power or torque with the various table values, a suitable desired value for the cooling medium quantity can then be determined. An alternative possibility to this consists in calculating the cooling medium quantity on the basis of a characteristic line. This characteristic line is preferably substantially linearly configured, but such that in the activated condition of the drive at least a minimum quantity of cooling medium is delivered.

For the final setting of the quantity of the cooling medium a number of possibilities are likewise conceivable. In accordance with a first variant, there is arranged within a delivery line for the cooling medium a so-called valve island having a plurality of different valves, wherein the control device opens that valve whose throughput corresponds to the desired cooling power. In the case of a second variant, in contrast, there is arranged in the delivery line for the cooling medium a proportional valve, which is controlled by the control and/or regulation means on the basis of a comparison of the current throughput quantity with the desired value predetermined by the determination means. For this purpose there is also arranged within the delivery line a further sensor for the detection of the cooling medium throughflow. This second variant is, with regard to the setting of the quantity of the cooling medium, somewhat more complicated, but however therefor ensures a more exact regulation of the quantity of the cooling medium.

If, instead of an electric motor, an air turbine or an air motor is employed as drive unit, the configuration of the control device differs primarily with regard to the detection of the removal power or the torque. Here, there arises in particular the possibility of using sensors which detect the pressure difference between drive air and return air, wherein the pressure difference, which is equal to the current power, can then be determined in an electronic evaluation unit. Further, sensors for detecting the speed of rotation may be arranged within the instrument.

The cooling medium made available may be for example air, water or a mixture in the form of a spray. For the case that a water-air spray is put to use as cooling medium, for regulation of the cooling power solely the quantity of the water may be set in the above-described manner. There would also, however, be the possibility of setting separately from one another both the air and also the water quantity, in order thus again to be able to regulate the cooling power better and more precisely.

Below the invention will be explained in more detail with reference to the accompanying drawings.

DETAILED DESCRIPTION OF THE INVENTION

Figure 1:
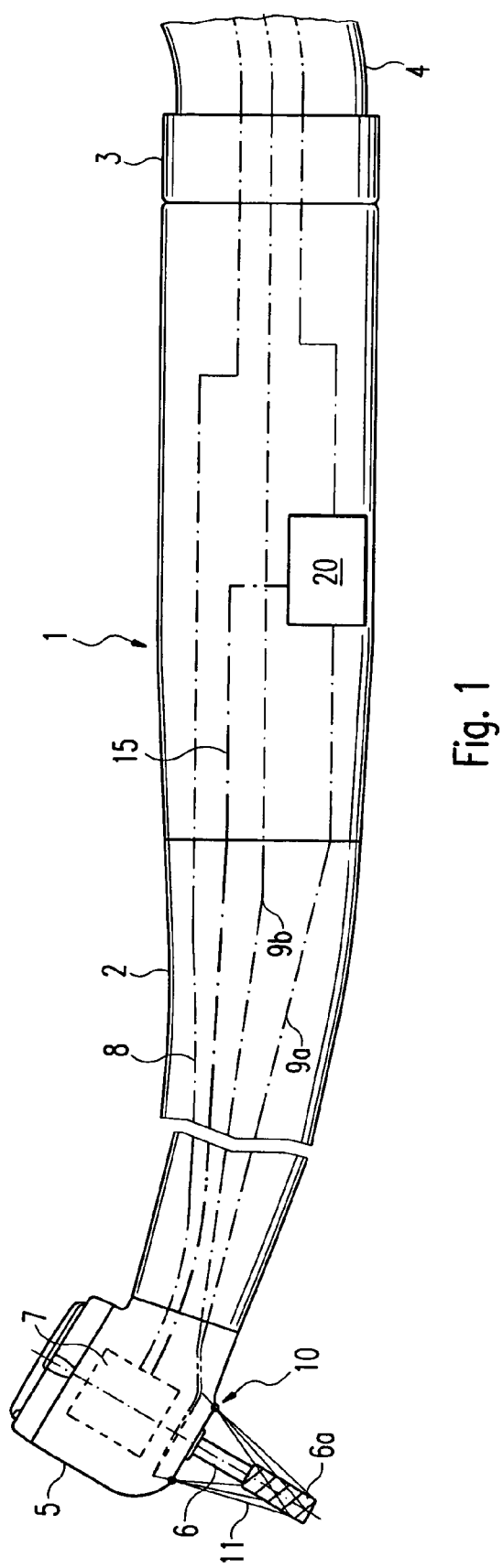
FIG. 1 depicts a dental treatment instrument, in side view.

The dental treatment instrument, provided in FIG. 1 overall with the reference sign 1, consists first of all of an elongate grip sleeve 2, which at its rearward end can be connected with a supply hose 4 via a connection part 3. The supply hose 4 leads to a (non-illustrated) supply device which makes available to the treatment instrument 1, via the hose 4, the necessary media for operation of the instrument. These media which are made available are in particular current, which for example can be put to use to drive a tool or for supplying an illumination device, and media for cooling the treatment site, such as e.g. air and/or water.

In the illustrated exemplary embodiment, an air turbine 7 is employed as a drive unit for driving a dental drill 6 which is arranged in the head region 5 of the treatment instrument 1. As a drive medium for this purpose, correspondingly compressed air is needed which is likewise delivered via the supply hose 4 and led to the turbine 7 by means of a supply line 8 which extends in longitudinal direction through the grip sleeve 2 of the treatment instrument 1.

The drill 6 driven by the turbine 7 is provided in its lower region with a drill head 6a which is suitable due to its abrasive characteristics for the removal of tooth material. Since heat arises at the treatment site as soon as the rotating drill 6 comes into contact with the tooth material, a cooling of the treatment site is necessary. In the illustrated exemplary embodiment this is effected with the aid of a spray mist 11 which emerges via nozzles 10 arranged in the head region 5 of the treatment instrument 1 and is directed towards the drill head 6a of the drill 6. If, now, the drill 6 is put into operation, thus at the same time also the spray mist 11 is directed towards the treatment site so that this is cooled.

The media for generating the spray mist, in particular thus air and water, are delivered via further supply lines 9a and 9b, which are likewise connected with the supply hose 4 and extend in longitudinal direction through the grip sleeve 2 of the instrument 1. In accordance with the present invention it is now however provided that the quantity of the issued spray is dependent upon the removal power of the drill 6 or upon the torque exercised by the drill 6. For this purpose there is arranged within the supply line 9a for the water employed for generating the spray mist, a control device 20, which via one or more connection lines 15 receives information regarding the current removal power or torque and correspondingly controls the quantity of water delivered to the head region 5. The manner of functioning of this control device 20 in accordance with the invention will be described below with reference to FIG. 2.

Significant components of the control device 20 are on the one hand detection means 21 for detecting current information concerning the drive unit of the treatment instrument, determination means 22 for determining a desired quantity for the cooling medium which is necessary at the current removal power or the current torque for making available an adequate cooling, and control/or regulation means 23 for setting the quantity of issued cooling medium.

Before the precise manner of functioning of all three components of the control device 20 is explained in more detail, it is to be remarked that in the illustrated exemplary embodiment it is presumed that a water-air mixture in the form of a spray is made available as cooling medium, wherein the water and the air are delivered via two separate supply lines 9a and 9b and—as schematically illustrated—are first mixed in the head region 5 of the treatment instrument to the desired spray. The regulation of the quantity of the cooling medium is effected in the illustrated exemplary embodiment exclusively in that the quantity of the delivered water is altered. This is sufficient for a control of the cooling power, since primarily the water is responsible for the cooling. It would, however, also be conceivable additionally, alongside the water quantity, also to set the air quantity in dependence upon the detected torque or the removal power.

Figure 2:
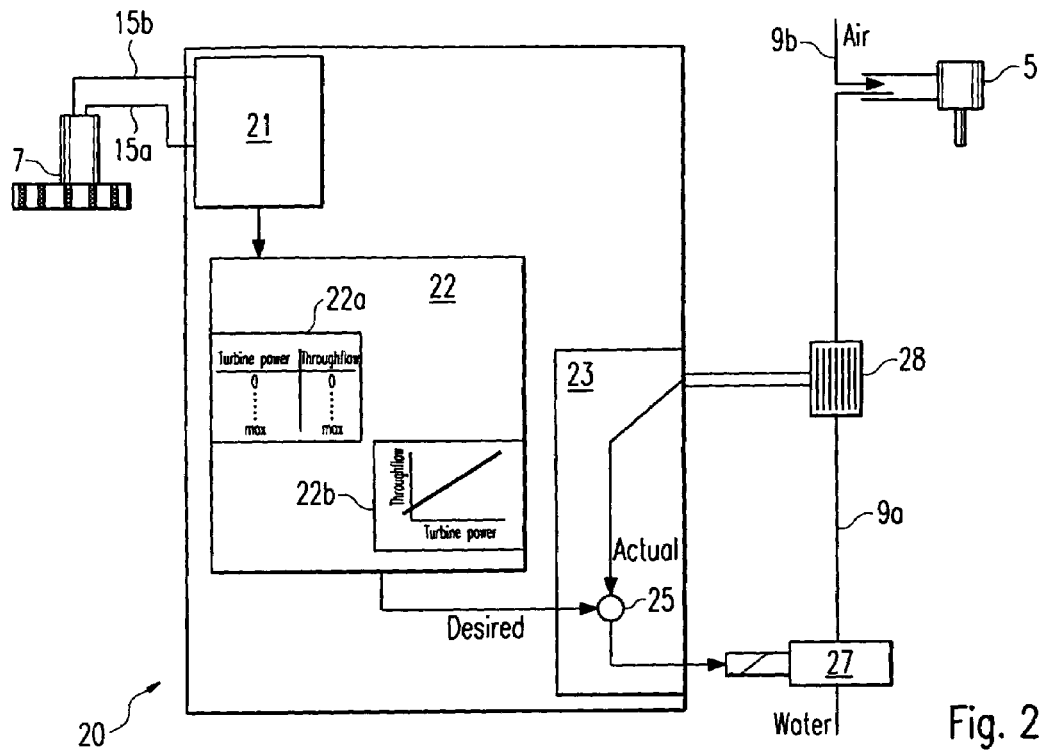
FIG. 2 depicts a first exemplary embodiment of a control device in accordance with the invention for regulation of the quantity of the cooling medium.

In the case of the exemplary embodiment illustrated in FIG. 2, there is provided as drive unit the air turbine 7 also illustrated in FIG. 1, which is connected via two connection lines 15a and 15b with the control device 20. More precisely stated, within the turbine 7, there are provided two sensors by means of which the torque of the turbine and its speed of rotation are detected. Both measurement values are then delivered via the lines 15a, 15b to the detection means 21 within the control device 22, which then calculates the current removal power of the turbine 7 in the following manner:

$$P_{Turbine} = Md \cdot n \cdot 2\pi$$

wherein $P_{Turbine}$ corresponds to the turbine power, Md the torque and n the speed of rotation. The information regarding the current removal power of the turbine 7 is then delivered to the determination means 22, which determine the necessary cooling power and pass to the control and/or regulation means 23 a corresponding desired value for the water quantity.

The determination of the desired value for the water quantity can be effected in two ways, which are both schematically illustrated in FIG. 2. In the case of a first exemplary embodiment there is placed within an electronic memory 22a of the determination means 22 a table in which the various turbine power values are linked with various throughput quantities. By means of a comparison of the currently determined turbine power with the various table values, a suitable desired value can then be determined. The information contained in the table is determined in advance on the basis of investigations, wherein here also the kind of the instrument or the characteristics of the drill are taken into account.

A second possibility for determination of the desired value for the water quantity consists in a calculation of this on the basis of the detected turbine power, whereby for this purpose a characteristic line can be put to use which is schematically illustrated with the reference sign 22b. In a simple variant, this characteristic line is configured to be linear, so that thus with increasing turbine power the water quantity made available also increases linearly. Thereby, however, the characteristic line is so selected that fundamentally in the case of an activated drive a certain minimum quantity of water is made available. Thus it is ensured that also in the case of small removal powers at least a certain basis cooling of the treatment site is effected. This basis cooling can, of course, also be provided in the case of determination of the necessary water quantity by means of the table 22a. Instead of the linear configuration, the characteristic line 22b may also be formed by means of a polynomial function.

The desired value for the water quantity determined in the above-described manner is then delivered to the control and/or regulation means, which in suitable manner carry out the regulation of the water quantity. In the case of the exemplary embodiment illustrated in FIG. 2, for this purpose there is arranged within the delivery line 9a for the water a proportional valve 27 which is variably controlled by means of a control signal of the control device 22, in order to set the water quantity. In order to make possible a regulation to the desired throughflow quantity which is as precise as possible there is further provided, downstream of the proportional valve 27 within the delivery line 9a, also another sensor 28, which detects the water throughflow by means of a determination of the differential pressure. The actual value determined in this way is then delivered to a regulation device 25 within the control and/or regulation means 23, which then controls the proportional valve 27 on the basis of a comparison of the actual value with the desired value. In this manner it is ensured that the water quantity made available exactly corresponds to the value determined by the determination means 22. The water quantity is then mixed with the air made available via the supply line 9b, in order to form the spray for cooling.

The cooling power is, in the above-described manner thus adapted quasi in real time to the current operating conditions. Preferably it is, however, provided that this automatic adaptation of the cooling power can at least temporally be deactivated and then the cooling medium quantity manually set by the user. In the case of a disruption, the user can thus still manually ensure that a sufficient cooling is effected.

Figure 3:
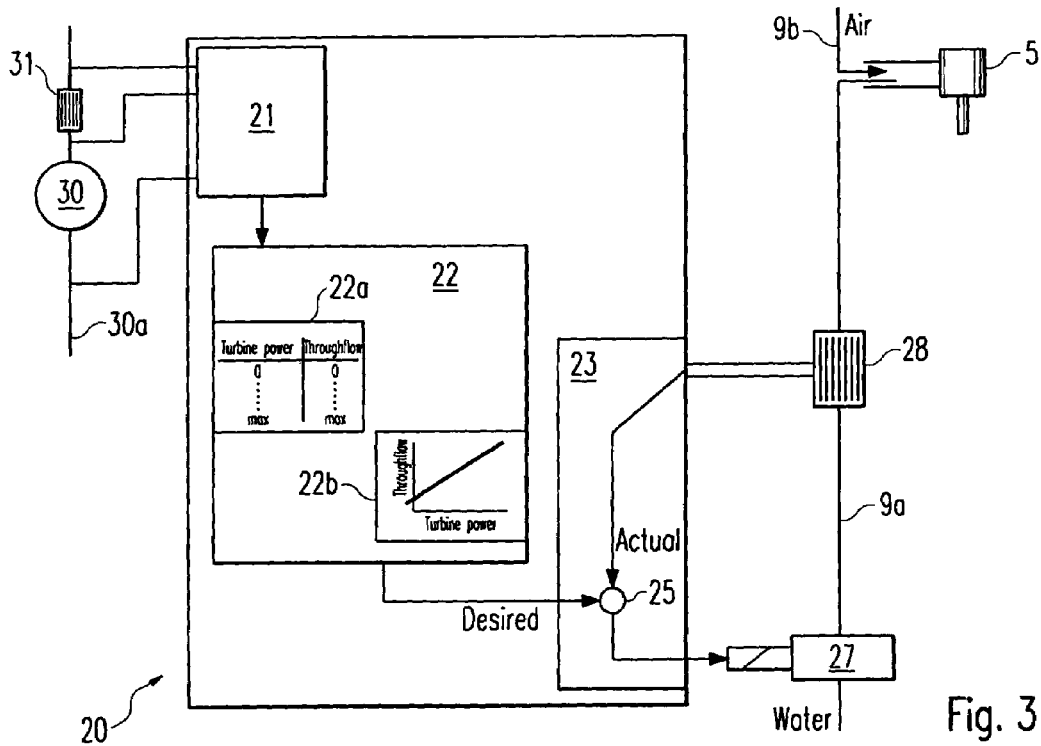
FIG. 3, FIG. 4 and FIG. 5 depict further variants of a control device configured in accordance with the invention.

In the case of the exemplary embodiment illustrated in FIG. 3 an air motor 30 is provided as drive unit instead of the turbine, the power or torque of which air motor is again monitored and then translated into a suitable quantity of cooling medium. For determining the power of the air motor 30 there is first of all provided within the compressed air line 30a a sensor which detects the current pressure p. By means of a further differential pressure sensor 31, which is arranged after the air motor 30, the throughflow quantity $V_{pkt}$ can beyond this be determined, whereby the power of the air motor $P_{Motor}$ is calculated as follows:

$$P_{Motor} = p \cdot V_{pkt}$$

The power determined in this manner by the detection means 21 is then in turn delivered to the determination means 22, which analogously to the above-described manner of proceeding, determine a desired value for the necessary water quantity. In turn, the desired value can be effected either on the basis of a comparison with table values or via a calculation within the scope of a characteristic line. Also the regulation of the water quantity is effected in the above-described manner, i.e. a proportional valve 27 is put to use which is controlled within a control loop.

Figure 4:
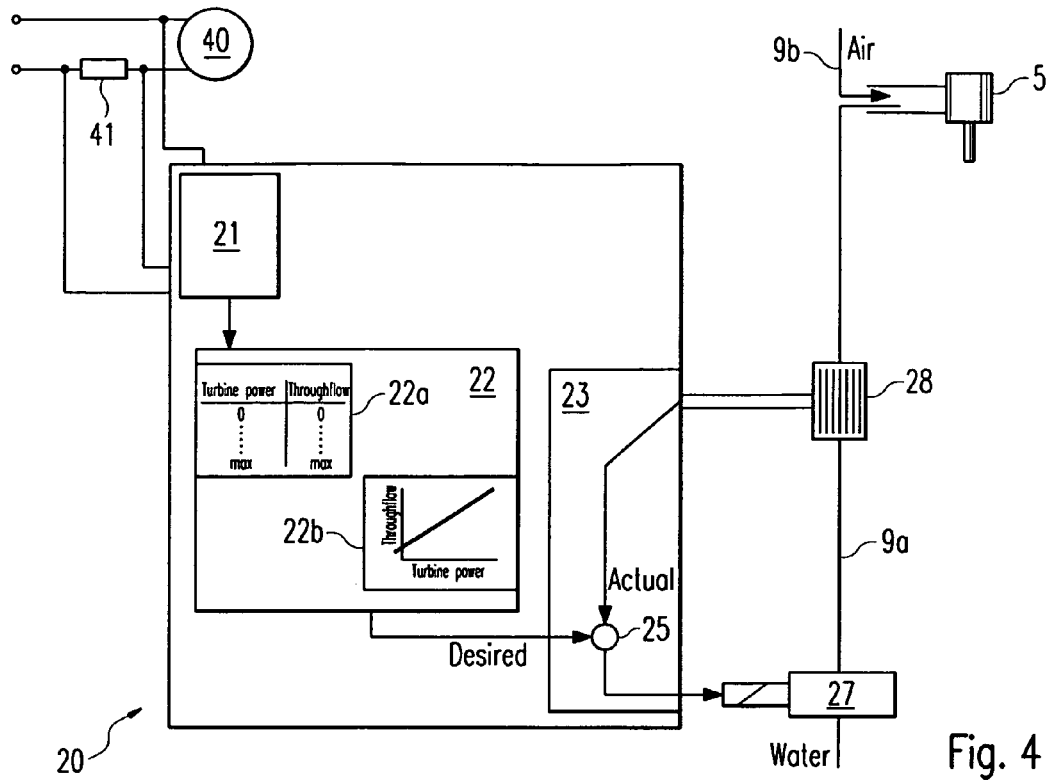

The exemplary embodiment illustrated in FIG. 4 differs with respect to the two exemplary embodiments of FIGS. 2 and 3 in that an electric motor 40 is employed as drive unit. In order to determine the motor power of the electric motor 40, now first of all the motor current $I_{Motor}$ is measured, which is effected by means of the determination of the voltage drop via a reference resistance 41. As further input value for the detection means 21, the motor voltage $U_{Motor}$ is also determined, so that then the motor power $P_{Motor}$ can be calculated in no manner as follows:

$$P_{Motor} = U_{Motor} \cdot I_{Motor}$$

Analogously to the exemplary embodiments of FIGS. 2 and 3 there is then effected in turn a determination of a suitable desired value, and regulation of the proportional valve 27 for making available a suitable water quantity.

Figure 5:
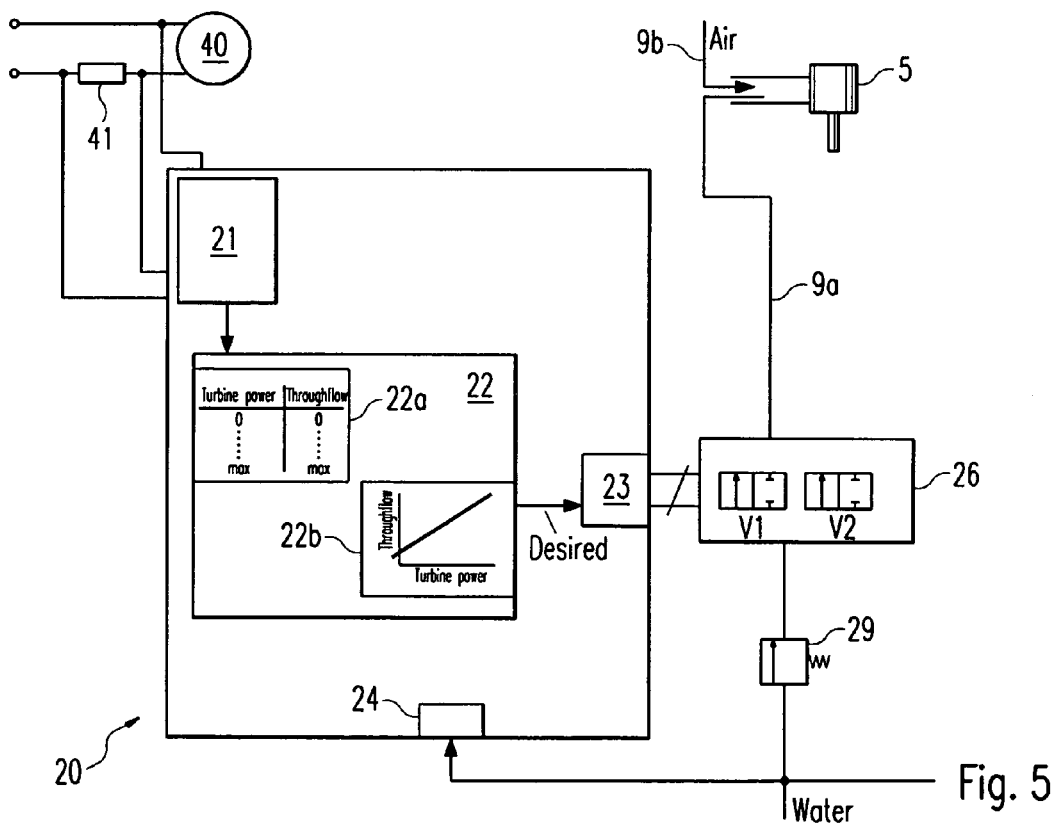

The final exemplary embodiment in FIG. 5 corresponds in substance to the exemplary embodiment of FIG. 4, in which an electric motor 40 is put to use as drive unit. Differences are present however, with regard to the regulation of the water quantity. Instead of the employment of a proportional valve with a simultaneous control loop, now a valve island 26 is provided which has a plurality of valves V1, V2 . . . which differ with regard to their throughput quantities. Depending upon the height of the desired value which is issued by the determination means 22, the control and/or regulation means then control the valve island 26 such that a valve with a suitable throughflow quantity is activated. A pressure limiter 29 arranged before the valve island 26 prevents a too high pressure reaching the valve island 26, further there is provided within the control device 20 a pressure monitoring device 24 in order to avoid operation of the apparatus with faulty water pressure. This control of the water quantity made available by means of the valve island 26 could, of course, also be put to use in the case of the exemplary embodiments with the turbine or with the air motor as drive unit.

Overall, the present invention thus opens up the possibility of adapting the quantity of cooling medium made available, and thus the cooling power, to the removal power. It is to be noted that instead of adaptation to the removal power it would also be conceivable to use for the control of the cooling power exclusively the torque exercised. Since the torque, with regard to its effect on the development of heat at the treatment site, has great similarity with the removal power, also in this case a suitable adaptation of the cooling power can be effected.

Further it is to be noted that alternatively to the illustrated exemplary embodiments, in which the control devices for regulation of the cooling power are in each case arranged in the treatment instrument, it could also be provided to arrange the control device in a supply device for the treatment instrument. In this case it is then provided that also different treatment instruments can be connected with the supply device. Since here also different cooling powers will be necessary, there is then preferably provided for each instrument a corresponding table with desired values for the necessary cooling power in dependence upon the current removal power. A user of the device then sends to the supply device manually the information as to which instrument is being used at the moment and which desired value table or characteristic line is to be employed. Of course it would also be conceivable that the supply device self-actingly recognizes the currently connected instrument via a coding and automatically refers to the suitable table or a characteristic line which could be used alternatively thereto.

In each case it is attained that the cooling power is set in suitable manner, so that on the one hand optimum working conditions prevail for a user of the treatment instrument and on the other hand a damage of the tooth being worked due to excessive heat development is avoided.

What is claimed is:

1. A dental treatment device, comprising:
   a tool driven by a drive unit;
   a conduit for delivering a cooling medium for a treatment site worked by the tool; and
   a control device comprising a detector for detecting a removal power of the tool, or a torque exercised by the tool, wherein the quantity of cooling medium delivered to the treatment site is variable, over a predetermined range, depending upon a measurement of removal power of the tool or upon a measurement of torque exercised by the tool, wherein the drive unit comprises an electric motor, and wherein the detector is configured to measure a motor current of the motor and a motor voltage of the motor and determine the removal power of the tool from a measurement of the motor current and a measurement of the motor voltage.

2. The treatment device according to claim 1, wherein the control device is further comprised of
   a device determining a desired value for a quantity for the cooling medium dependent upon information provided from the detector, and
   a controller and/or regulator for setting the quantity of the cooling medium issued dependent upon the determined desired quantity.

3. The treatment device according to claim 2, wherein the device determining the desired value for the quantity of the cooling medium compares the removal power or the torque detected by detector with predetermined values from a desired value table.

4. The treatment device according to claim 3, wherein in an activated condition of the drive unit a minimum quantity of cooling medium is delivered.

5. The treatment device according to claim 2, wherein the device determining the desired value for the quantity of the cooling medium calculates the desired value in correspondence with a characteristic line.

6. The treatment device according to claim 5, wherein the characteristic line is substantially linear.

7. The treatment device according to claim 2, wherein the cooling medium is air, water, or a mixture of air and water.

8. The treatment device according to claim 7, wherein the controller and/or regulator control a valve unit located in a delivery line for the cooling medium on the basis of the desired value determined by the device for determining the desired value for the quantity of cooling medium.

9. The treatment device according to claim 8, wherein the valve unit is a device with a plurality of valves connected in parallel, the controller and/or regulator activating one of the valves, the throughput of which corresponds substantially to the desired value determined by the device for determining the quantity of cooling medium.

10. The treatment device according to claim 8, wherein the valve unit is a proportional valve.

11. The treatment device according to claim 10, wherein there is arranged in the delivery line for the cooling medium a sensor for detecting a throughflow quantity of the cooling medium, the controller or regulator controlling the proportional valve on the basis of a comparison between the desired value and a detected throughflow quantity.

12. The treatment device according to claim 7, wherein the cooling medium is a spray.

13. The treatment device according to claim 12, wherein the quantity of the cooling medium is set solely by altering the water quantity.

14. The treatment device according to claim 12, wherein the quantity of the cooling medium is set by altering both the air quantity and also the water quantity.

15. The treatment device according to claim 1, wherein the control device is integrated in a treatment instrument which has the drive unit and the tool.

16. The treatment device according to claim 1, wherein the control device is arranged in a supply unit for a treatment instrument.

17. The treatment device according to claim 16, wherein the supply unit can be connected with different treatment instruments having different drive units and/or tools.

18. The treatment device according to claim 17, wherein the supply unit automatically recognizes the connected treatment instrument.

19. The treatment device according to claim 1, wherein setting of the quantity of the cooling medium in dependence upon the removal power of the tool or the torque exercised by the tool can be deactivated at least temporarily.

20. A method of operating a dental treatment device, comprising:
    delivering a cooling medium to a treatment site worked with a tool wherein a quantity of the cooling medium delivered to the treatment site is variable, through a predetermined range, depending upon a measurement of removal power of the tool or upon a measurement of torque exercised by the tool, wherein the tool is driven by a drive unit comprised of an electric motor, and wherein a detector of the dental treatment device measures a motor current of the motor and a motor voltage of the motor and determines the removal power of the tool from a measurement of the motor current and a measurement of the motor voltage.

* * * * *